US009808352B2

(12) United States Patent
Suddaby et al.

(10) Patent No.: US 9,808,352 B2
(45) Date of Patent: Nov. 7, 2017

(54) EXPANDABLE SPINAL INTERBODY SPACER AND METHOD OF USE

(71) Applicant: K2M, Inc., Leesburg, VA (US)

(72) Inventors: Loubert Suddaby, Orchard Park, NY (US); Larry McClintock, Gore, VA (US); Adam Wassinger, Portland, OR (US); Scott Jones, McMurray, PA (US); Jennifer Moore, Summit Point, WV (US); John Donohoe, Sterling, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 15/427,774

(22) Filed: Feb. 8, 2017

(65) Prior Publication Data

US 2017/0143506 A1    May 25, 2017

Related U.S. Application Data

(62) Division of application No. 14/510,598, filed on Oct. 9, 2014, now Pat. No. 9,585,762.

(51) Int. Cl.
*A61F 2/44* (2006.01)
*A61F 2/46* (2006.01)
*A61F 2/30* (2006.01)

(52) U.S. Cl.
CPC .......... *A61F 2/442* (2013.01); *A61F 2/30771* (2013.01); *A61F 2/4455* (2013.01); *A61F 2/4611* (2013.01); *A61F 2002/30398* (2013.01); *A61F 2002/30405* (2013.01); *A61F 2002/30471* (2013.01); *A61F 2002/30522* (2013.01); *A61F 2002/30579* (2013.01); *A61F 2002/30787* (2013.01); *A61F 2002/30797* (2013.01); *A61F 2002/30904* (2013.01); *A61F 2002/4475* (2013.01); *A61F 2002/4627* (2013.01)

(58) Field of Classification Search
None
See application file for complete search history.

(56) References Cited

U.S. PATENT DOCUMENTS 5,554,191 A    9/1996  Lahille et al.
6,102,950 A    8/2000  Vaccaro
(Continued)

OTHER PUBLICATIONS

International Search Report for PCT/US2015/054969 dated Jan. 8, 2016.

*Primary Examiner* — Sameh Boles
(74) *Attorney, Agent, or Firm* — Carter, DeLuca, Farrell & Schmidt, LLP

(57) ABSTRACT

An expandable spinal implant configured for positioning within a space between adjacent vertebral bodies includes an upper body, a lower body, a ratchet mechanism, and a plurality of bone screws. The upper body and lower body are pivotably affixed at a first end and are capable of movement relative to each other. The ratchet mechanism is slidably disposed on one of the upper and lower body and is capable of engaging the opposite one of the upper and lower body thereby permitting movement of the upper and lower body relative to each other in a first direction, but not in a second direction. An insertion instrument capable of being attached to the expandable spinal instrument and a method of performing spinal surgery is also disclosed.

8 Claims, 18 Drawing Sheets

(56) References Cited

U.S. PATENT DOCUMENTS

| | | |
|---|---|---|
| 6,159,244 A | 12/2000 | Suddaby |
| 6,174,334 B1 | 1/2001 | Suddaby |
| 6,176,882 B1 | 1/2001 | Biedermann et al. |
| 6,190,414 B1 | 2/2001 | Young et al. |
| 6,332,895 B1 | 12/2001 | Suddaby |
| 6,491,724 B1 | 12/2002 | Ferree |
| 6,716,247 B2 | 4/2004 | Michelson |
| 6,808,537 B2 | 10/2004 | Michelson |
| 6,962,606 B2 | 11/2005 | Michelson |
| 6,972,035 B2 | 12/2005 | Michelson |
| 7,008,453 B1 | 3/2006 | Michelson |
| 7,044,971 B2 | 5/2006 | Suddaby |
| 7,217,293 B2 | 5/2007 | Branch, Jr. |
| 7,655,027 B2 | 2/2010 | Michelson |
| 7,678,148 B2 | 3/2010 | Peterman |
| 8,137,405 B2 | 3/2012 | Kostuik et al. |
| 8,366,777 B2 | 2/2013 | Matthis et al. |
| 8,496,706 B2 | 7/2013 | Ragab et al. |
| 8,518,114 B2 | 8/2013 | Marik |
| 8,663,329 B2 | 3/2014 | Ernst |
| 8,845,733 B2 | 9/2014 | O'Neil et al. |
| 9,572,680 B2 | 2/2017 | Theofilos et al. |
| 9,585,762 B2 | 3/2017 | Suddaby et al. |
| 2002/0068976 A1 | 6/2002 | Jackson |
| 2004/0087947 A1 | 5/2004 | Lim et al. |
| 2004/0254643 A1 | 12/2004 | Jackson |
| 2005/0015149 A1 | 1/2005 | Michelson |
| 2005/0125061 A1 | 6/2005 | Zucherman et al. |
| 2006/0122701 A1 | 6/2006 | Kiester |
| 2011/0172774 A1 | 7/2011 | Varela |
| 2011/0319997 A1 | 12/2011 | Glerum et al. |
| 2012/0310350 A1 | 12/2012 | Farris et al. |
| 2013/0158663 A1 | 6/2013 | Miller et al. |
| 2013/0158664 A1 | 6/2013 | Palmatier et al. |
| 2013/0197642 A1 | 8/2013 | Ernst |
| 2013/0211526 A1 | 8/2013 | Alheidt et al. |
| 2015/0057755 A1* | 2/2015 | Suddaby ............. A61F 2/4425 623/17.16 |

* cited by examiner

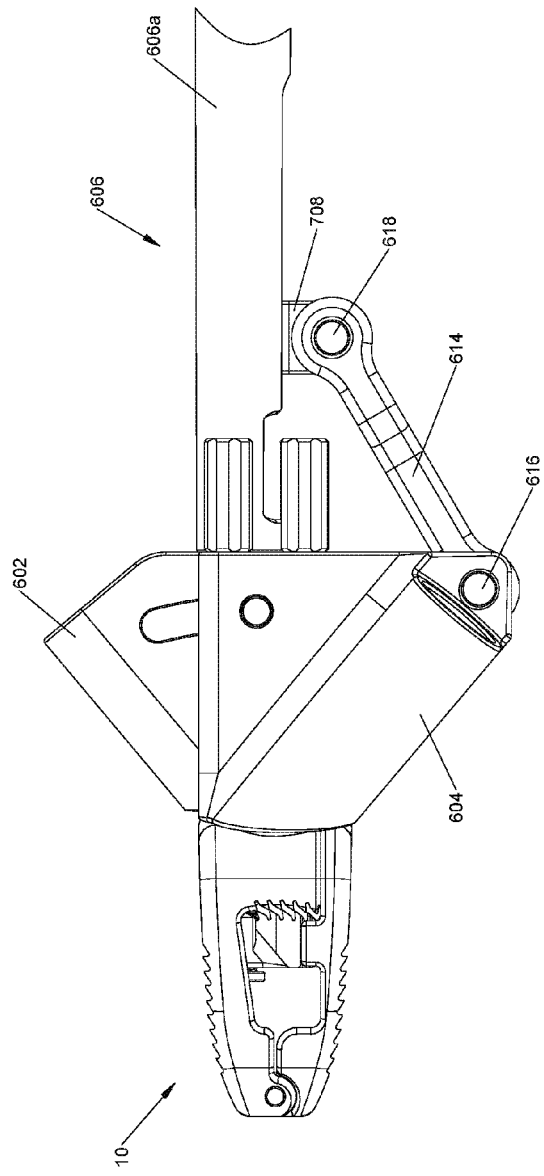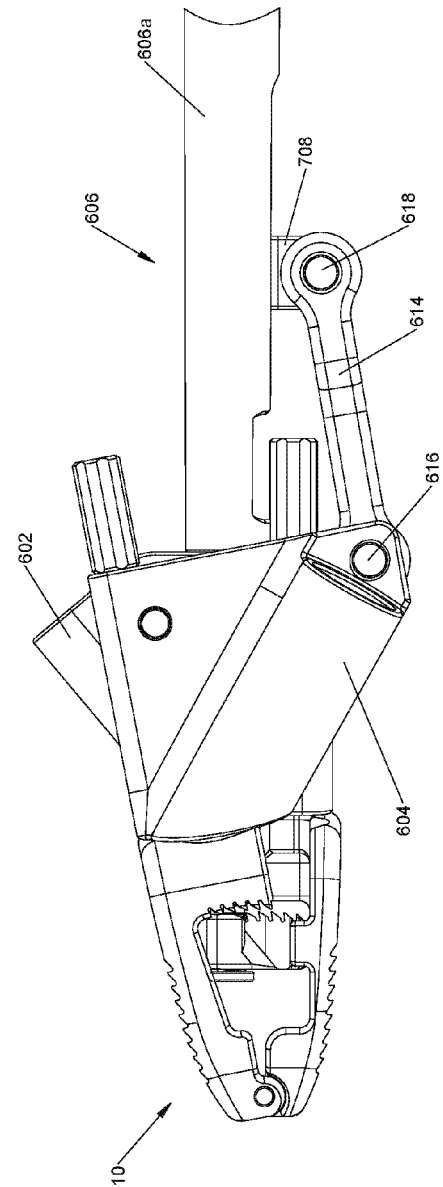

EXPANDABLE SPINAL INTERBODY SPACER AND METHOD OF USE

CROSS-REFERENCE TO RELATED APPLICATION

This application is a division of U.S. patent application Ser. No. 14/510,598, filed on Oct. 9, 2014, the entire contents of which are incorporated by reference herein.

BACKGROUND

Technical Field

The present disclosure relates generally to devices and methods for treating spinal conditions, and in particular, to expandable spinal implants configured for positioning within an intervertebral space.

Background of the Disclosure

After a partial or complete discectomy, the normally occupied space between adjacent vertebral bodies may collapse and/or become misaligned due to the absence of all or a part of the intervertebral disc. In these situations, a physician may insert one or more prosthetic spacers between the affected vertebrae to maintain normal disc spacing and/or the normal amount of lordosis in the affected region.

Typically, a prosthetic implant is inserted between the adjacent vertebrae and may include pathways that permit bone growth between the adjacent vertebrae until they are fused together. However, there exists a possibility that conventional prosthetic implants may be dislodged or moved from their desired implantation location due to movement by the patient before sufficient bone growth has occurred.

Additionally, achieving the desired lordosis can be difficult given the limitations of typical prosthetic implants once they are implanted.

Therefore, a need exists for a spinal implant that provides a desired amount of lordosis, allows for bone growth between adjacent vertebrae, maintains the space between adjacent vertebrae during bone ingrowth, and resists dislocation from its implantation site.

SUMMARY

In accordance with the present disclosure, a spinal implant including an upper body, a lower body, a ratchet mechanism, and a plurality of bone screws is provided. The upper body and the lower body are pivotably affixed at a first end and are capable of movement relative to each other. Each of the upper body and the lower body is dimensioned to be installed between two vertebral bodies. The outer surfaces of each of the upper body and the lower body are adapted to engage a corresponding end plate of the two vertebral bodies. Screw holes are defined through the outer surface and an adjacent side surface of the upper body and the outer surface and an adjacent side surface of the lower body. The screw holes are oriented towards a respective adjacent one of the two vertebral bodies at an oblique angle. The ratchet mechanism is slidably disposed on one of the upper and lower bodies. The ratchet mechanism is capable of engaging the opposite one of the upper and lower bodies thereby permitting movement of the upper and lower bodies relative to each other in a first direction, but not in a second direction. The bone screws are insertable through corresponding screw holes of the upper body and the lower body and are attachable to bone.

In aspects, the spinal implant further includes a first lumen defined through the upper body and a second lumen defined through the lower body.

In aspects, the spinal implant further includes a plurality of ridges disposed on an outer surface of each of the upper body and the lower body. The plurality of ridges is adapted to engage a respective one of the two vertebral bodies.

In aspects, the spinal implant further includes a pair of screw holes disposed on the lower body and a single screw hole disposed on the upper body.

In aspects, the spinal implant further includes a ratchet screw rotatably supported within an annular groove defined within the lower body. The ratchet screw includes a head and threaded shank extending therefrom and is threadably engaged within a threaded through-hole defined through the ratchet mechanism. Rotation of the ratchet screw in a first direction effectuates movement of the ratchet mechanism in a first direction, and rotation of the ratchet screw in a second, opposite, direction effectuates movement of the ratchet mechanism in a second, opposite, direction.

In aspects, the spinal implant further includes a plurality of threaded bores defined through an end surface of each of the upper body and lower body. The plurality of threaded bores is configured to engage an insertion instrument capable of inserting the spinal implant between the two vertebral bodies.

In aspects, the spinal implant further includes a locating pin disposed within a through-bore defined through a side face of the lower body and a locating bore defined through the ratchet mechanism. The through-bore and locating bore are in coaxial alignment. The locating pin is in frictional engagement with the through-bore thereby retaining the locating pin therein and the ratchet mechanism is translatably supported on the locating pin.

In aspects, the spinal implant further includes a pair of legs extending from an underside of the ratchet mechanism. The pair of legs is configured to engage a corresponding pair of channels disposed on the interior surface of the upper body thereby translatably supporting the ratchet mechanism therein.

In aspects, the upper body and lower body are pivotably coupled via a hinge pin disposed within an aperture defined on the first end of the lower body and a through-hole defined on the first end of the upper body. The hinge pin is frictionally engaged with one of a first or second end of the aperture thereby retaining the hinge pin therein.

In aspects, the ratchet mechanism is slidably disposed on an interior surface of the upper body. The ratchet mechanism further includes a first plurality of teeth disposed thereon.

In aspects, the lower body includes a second plurality of teeth disposed on an interior surface thereon opposite the ratchet mechanism of the upper body. The second plurality of teeth is configured to engage the first plurality of teeth of the ratcheting mechanism.

In aspects, the first and second pluralities of teeth are oriented such that the first and second pluralities of teeth are slidably engaged in a first direction, and are prohibited from movement relative to each other in a second direction, thereby locking the position of the upper body and the lower body relative to each other.

A method of performing surgery provided in accordance with the present disclosure includes providing a spinal implant comprising an upper body, a lower body, a ratchet mechanism, and a plurality of bone screws is provided. The upper body and the lower body are pivotably affixed at a first end and are capable of movement relative to each other. Each of the upper body and the lower body is dimensioned to be installed between two vertebral bodies. The outer surfaces of each of the upper body and the lower body are adapted to engage a corresponding end plate of the two vertebral bodies. Screw holes are defined through the outer surface and an adjacent side surface of the upper and the outer surface and an adjacent side surface of the lower body. The screw holes are oriented towards a respective adjacent one of the two vertebral bodies at an oblique angle. The ratchet mechanism is slidably disposed on one of the upper and lower bodies. The ratchet mechanism is capable of engaging the opposite one of the upper and lower bodies thereby permitting movement of the upper and lower bodies relative to each other in a first direction, but not in a second direction. The bone screws are insertable through corresponding screw holes of the upper body and lower body and are attachable to bone. The method further includes positioning the upper body and lower body in a first, approximated position relative each other, preparing an intervertebral space between first and second vertebral bodies to receive the spinal implant, inserting the spinal implant into the prepared intervertebral space, articulating the upper body and lower body relative to each other to effectuate a desired lordosis of a spine of the patient, inserting a plurality of bone screws through the plurality of screw holes of the upper body and lower body and into each of the respective two vertebral bodies, and locking the ratchet mechanism to lock the position of the upper body and lower body relative to each other.

In aspects, inserting the spinal implant includes first securing the spinal implant to an insertion device.

In aspects, locking the ratchet mechanism includes rotating a ratchet screw disposed within an annular groove defined within the upper body in a first direction, wherein the ratchet screw includes a head and a threaded shank extending therefrom. The ratchet screw is threadably engaged within a threaded through-hole defined through the ratchet mechanism. Rotating the ratchet screw effectuates movement of the ratchet mechanism in a first direction thereby causing the ratchet mechanism to engage the lower body and lock the position of the lower body relative to the upper body.

In aspects, positioning the upper body and lower body in a first, approximated, position includes engaging a first plurality of teeth defined on a surface of the ratchet mechanism with a second plurality of teeth defined on an opposing surface of the lower body, thereby permitting articulation of the upper body relative to the lower body in a first direction, but not in a second direction.

In aspects, locking the ratchet mechanism further includes further rotating the ratchet screw the first direction, causing the first and second pluralities of teeth to further engage, thereby locking the position of the upper body and the lower body relative to each other.

In aspects, the method further includes packing a lumen defined in each of the upper body and lower body with bone in-growth material.

In aspects, the method further includes packing a lumen defined in each of the upper body and lower body with drugs.

In aspects, positioning the upper body and lower body includes positioning the upper body and lower body in a desired articulated position relative to each other.

BRIEF DESCRIPTION OF THE DRAWINGS

The above and other aspects, features, and advantages of the present disclosure will become more apparent in light of the following detailed description when taken in conjunction with the accompanying drawings in which:

FIG. 17 is a side view of the distal end of the insertion instrument of FIG. 12 and the expandable spinal implant of FIG. 1, shown in an approximated state; and FIG. 18 is a side view of the distal end of the insertion instrument of FIG. 12 and the expandable spinal implant of FIG. 1, shown in an articulated state.

DETAILED DESCRIPTION OF THE EMBODIMENTS

Figure 1:
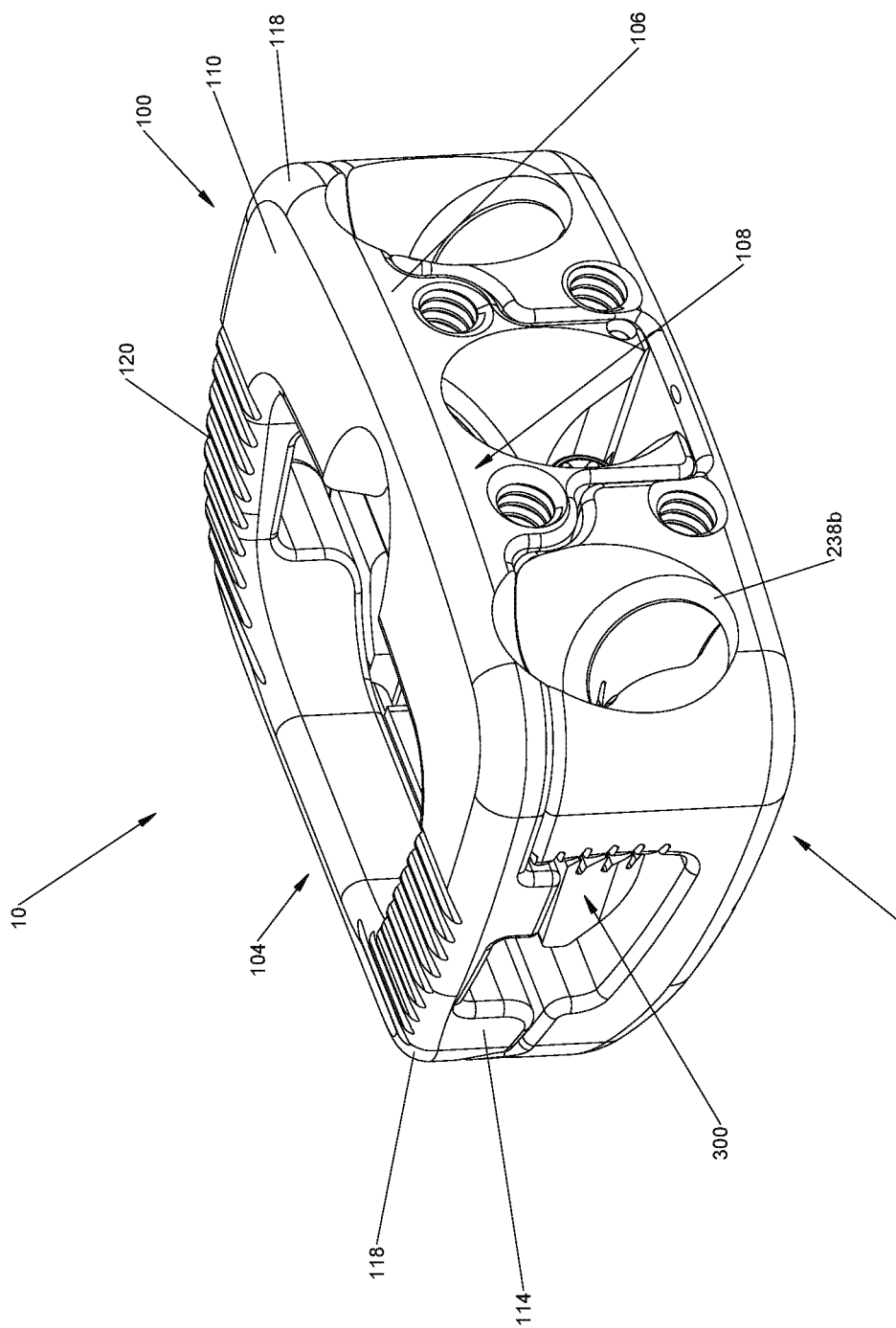
FIG. 1 is a rear, perspective view of an expandable spinal implant provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Referring now to the drawings, FIG. 1 illustrates an embodiment of expandable spinal implant 10 provided in accordance with the present disclosure. Expandable spinal implant 10 includes an upper body 100, a lower body 200, and a ratchet 300. Now, referring additionally to FIG. 2, a ratchet screw 400, an insertion instrument 500 (FIG. 7), a washer 11, a locating pin 12, and a hinge pin 13 are illustrated. Upper and lower bodies 100, 200 cooperate to define a two part expandable spinal implant configured for positioning between adjacent vertebral bodies. Bone screws 14 (FIGS. 6A-C) are configured for securing each of upper and lower bodies 100, 200 to the adjacent vertebral bodies, thereby substantially retaining expandable spinal implant 10 in position relative to the adjacent vertebral bodies. Ratchet 300 and ratchet screw 400 cooperate to provide a locking mechanism to lock upper and lower bodies 100, 200 in an articulated position relative to each other, thereby effectuating adjustment of lordosis of the spine. Each of these components along with the assembly and insertion of expandable spinal implant 10 into the intervertebral space between adjacent vertebral bodies will be described in turn hereinbelow.

The various components of expandable spinal implant 10, or portions thereof, may be formed from various similar or different materials, depending on a particular purpose. In particular, upper and lower bodies 100, 200 may be formed from a metallic material (e.g., titanium, titanium alloy, or cobalt chrome (CoCr)) or a non-metallic material (e.g., polymeric materials such as polyetheretherketone (PEEK), nylon absorbable polymers such as polyglycolides, polylactides, polycaprolactone, etc., or organic materials such as bone). Bone screw 14 may be formed from titanium, titanium alloy, CoCr or other suitable metal that is compatible with expandable spinal implant 10.

Figure 2:
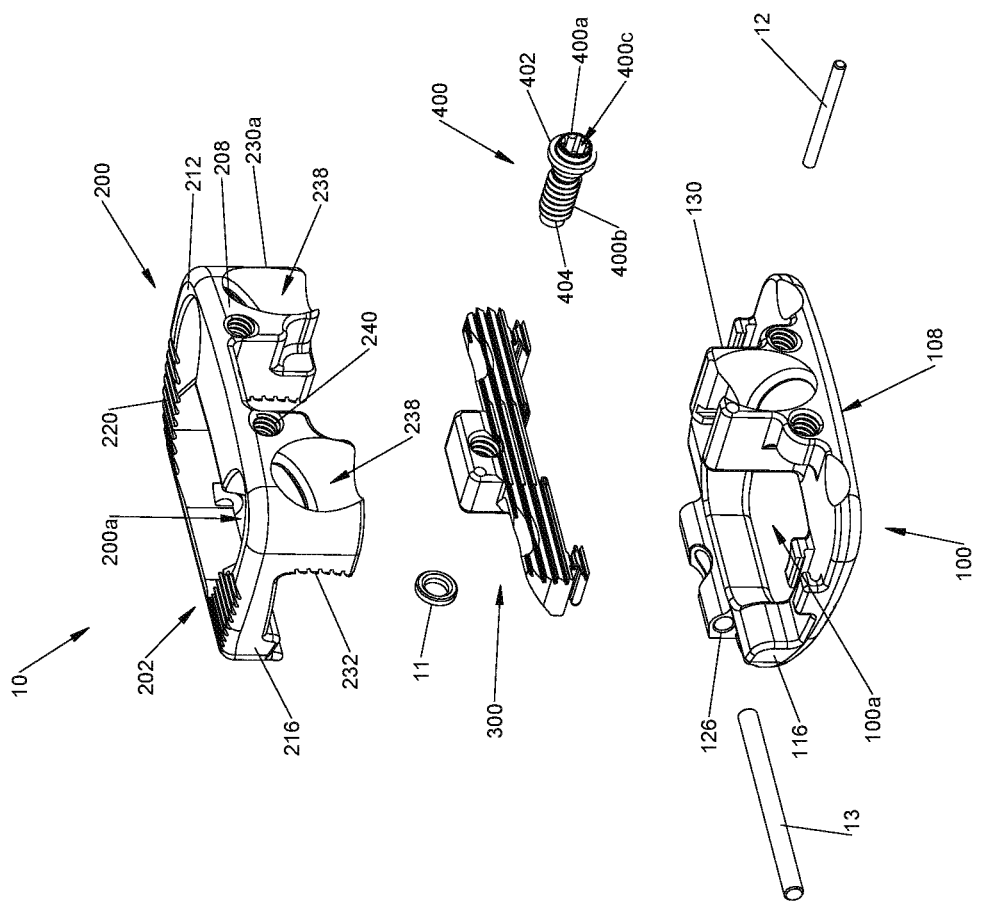
FIG. 2 is an exploded view, with parts separated, of the expandable spinal implant of FIG. 1.
Figure 2A:
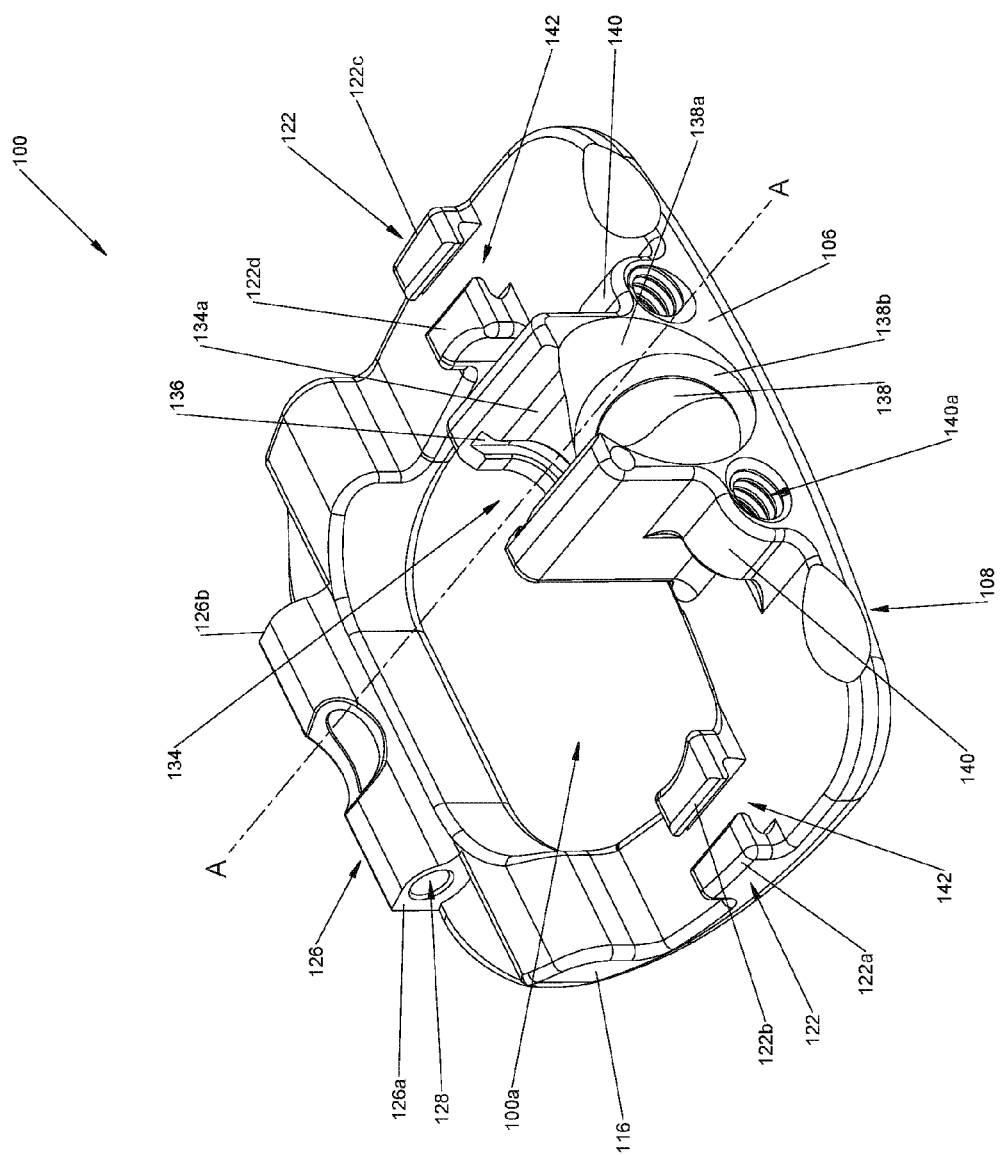
FIG. 2A is a perspective view of an upper body of the expandable spinal implant of FIG. 1.

With reference to FIGS. 1, 2, and 2A, upper body 100 is illustrated as having generally a D-shape; however, it is contemplated that upper body 100 may include other shapes, such as square, rectangular, circular, or the like. Upper body 100 includes a substantially contoured first end surface 102 (FIG. 4) at a distal or leading end 104 and a second end surface 106 opposite thereto at a proximal or trailing end 108. Upper body 100 extends between the first and second end surfaces 102, 106 to define respective top and bottom surfaces 110, 112, as well as opposed side surfaces 114, 116. As illustrated in FIGS. 1 and 2, top and bottom surfaces 110, 112, engage side surfaces 114, 116, respectively, to provide a substantially quadrilateral cross-section with rounded corners 118 on an upper end thereof. Although upper body 100 is illustrated as having rounded corners 118 extending around the entire perimeter thereof, it is contemplated that only the intersection of the proximal and distal end surfaces 102, 106 and top surface 110 includes rounded corners 118. Top surface 110 is generally shown as approximating bottom surface 112 in a direction from trailing end 108 to leading end 104; however, it is contemplated that top surface 110 may be parallel to bottom surface 112. First lumen 100a is defined through top and bottom surface 110, 112. Although shown as generally having a complimentary shape to that of body 100, it is contemplated that first lumen 100a may have any suitable shape, such as square, oval, circular, or the like.

With reference to FIG. 1, upper surface 110 defines a plurality of ridges 120 arranged thereon. Ridges 120 are configured to frictionally engage an adjacent surface of a vertebral body (i.e., a vertebral endplate) to maintain expandable spinal implant 10 in a position relative to the adjacent vertebral body and to inhibit expandable spinal implant 10 from backing out of the intervertebral space since the ridges 120 will bite into the adjacent vertebral endplate.

Referring now to FIGS. 2 and 2A, an illustration of the underside of upper body 100 is shown. Bottom surface 112 is generally planar and includes a plurality of retainers 122 extending normally therefrom. Retainers 122 include tabs 122a, 122b, 122c, and 122d, having a generally L-shaped profile (i.e., a vertical member intersecting a horizontal member) and are configured and/or adapted to retain feet 302b (FIG. 3) of ratchet 300 therein. Retainers 122 are arranged in opposed pairs such that tabs 122a and 122b are disposed adjacent to side surface 116 and tabs 122c and 122d are disposed adjacent to side surface 114 (FIG. 1), thereby forming a T-shaped channel 142 configured to engage feet 302b ratchet 300 such that ratchet 300 is translatably supported therein. Although generally shown as being co-planar with side surfaces 114, 116, it is contemplated that tabs 112a, 122c may be recessed from each of side surfaces 114, 116 or protruding therefrom.

Hinge 126 extends normal from bottom surface 112 of upper body 100 adjacent to leading end 104 (FIG. 1). Hinge 126 is centrally located between each of side surfaces 114 (FIG. 1), 116 and includes end surfaces 126a and 126b. Through-hole 128 is defined through each of end surfaces 126a and 126b and is configured and/or adapted to receive hinge pin 13 such that hinge pin is rotatably supported therein. Although generally shown as extending partially towards each of side surfaces 114, 116, it is contemplated that end surfaces 126a, 126b may be co-planar with side surfaces 114, 116 and a recess may be defined within a center region of hinge 126.

Lug 130 extends normal from bottom surface 112 of upper body 100 and is adjacent to trailing end 108. Lug 130 is centrally located between each of side surfaces 114, 116 and includes leading face 132. Opening 134 is defined through each of leading face 132 and second end surface 106 and defines an inner surface 134a and longitudinal axis A-A. Annular groove 136 is defined in the leading end of inner surface 134a and is configured to receive flange 402 of ratchet screw 400 thereby rotatably supporting ratchet screw 400 and preventing ratchet screw 400 from advancing axially along longitudinal axis A-A. Screw hole 138 extends through lug 130. Screw hole 138 is obliquely angled relative to second end surface 106 (e.g., screw hole 138 extends in a non-perpendicular orientation relative to second end surface 106) thereby directing bone screw 14 (FIGS. 6A-6C) therethrough at a similar oblique angle towards one of the vertebral bodies for engagement of bone screw 14 within the vertebral body despite upper body 100 being vertically displaced (e.g., vertically offset, relative to the vertebral body into which the bone screw 14 extending through screw hole 138 is to engage). Screw hole 138 further defines counterbore 138a disposed therein terminating in lip 138b. Lip 138b is configured and/or adapted to engage thread 16b of head 16 of bone screw 14 thereby retaining bone screw 14 within screw hole 138 and preventing bone screw 14 from backing out of screw hole 138. In particular, bone screw 14 may be formed from a titanium alloy (e.g., Ti-6Al-4V) and the lip 138b is formed of a softer compatible material, such as unalloyed titanium. As bone screw 14 is advanced through screw hole 138, the thread 16b engages the lip 138b. As the lip 138b is formed from a softer material than the bone screw 14, advancement of the bone screw 14 through the screw hole 138 results in the thread 16*b* deforming the lip 138*b* such that the bone screw 14 resists backing out of the screw hole 138.

Figure 7:
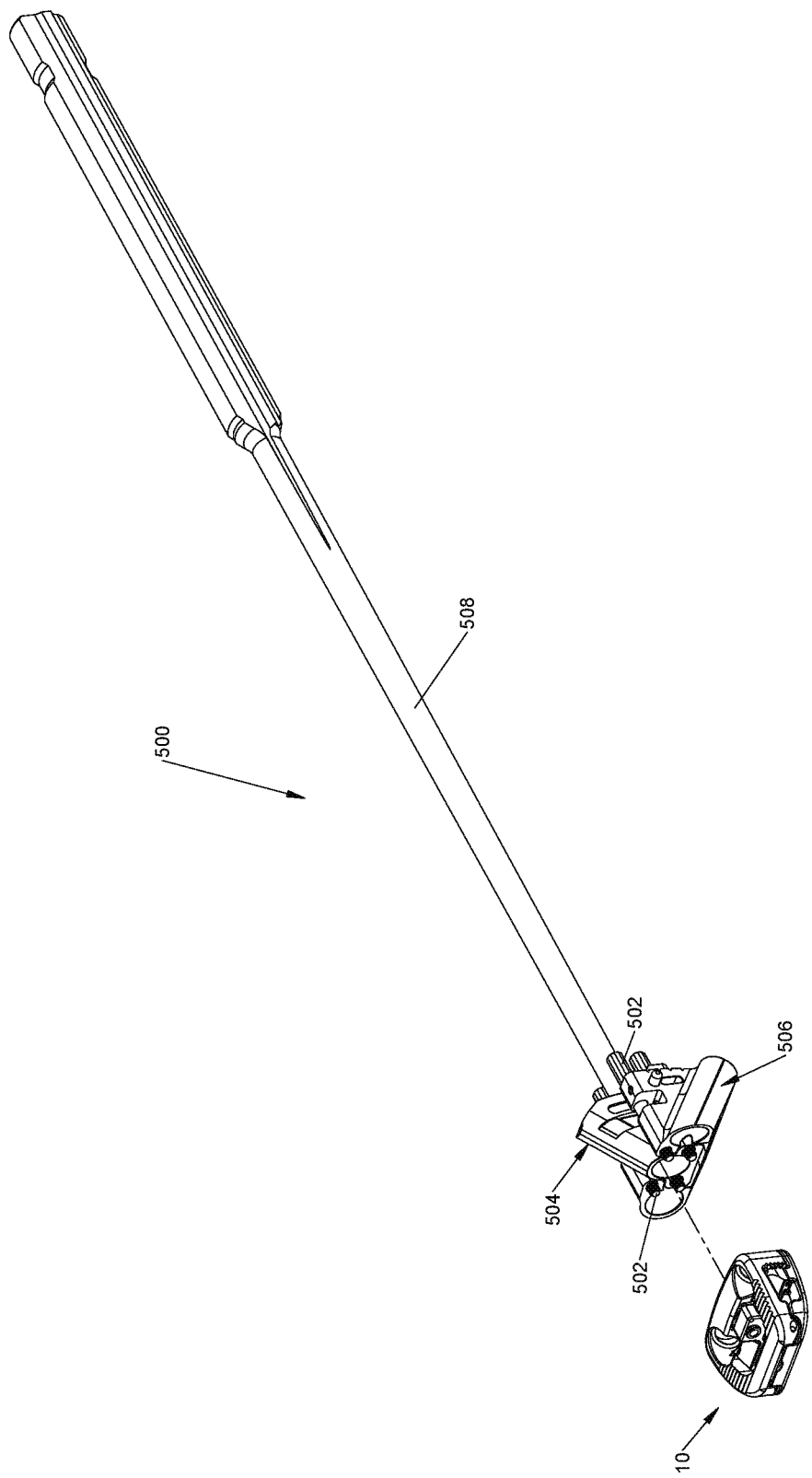
FIG. 7 is a perspective view of an insertion instrument and the expandable spinal implant of FIG. 1 in accordance with the present disclosure.

Disposed on either side of lug 130 is a plurality of bosses 140. Each boss 140 includes a threaded bore 140*a* defined therethrough configured and/or adapted to engage guide screws 502 of insertion instrument 500 (FIG. 7).

Through-bore 144 (FIG. 2A) is defined through second end surface 106 and leading face 132 on an upper end of lug 130 and is configured and or adapted to receive locating pin 12 such that locating pin 12 is frictionally engaged therein. Through-bore 144, locating pin 12, and locating bore 310 (FIG. 3) cooperate to translatably support ratchet 300 on locating pin 12.

With reference to FIG. 2, lower body 200 is illustrated as having a shape complimentary to that of upper body 100. Lower body 200 includes a substantially contoured first end surface 202 at a distal or leading end 204 (FIG. 5) and a second end surface 206 opposite thereto at a proximal or trailing end 208. Lower body 200 extends between the first and second end surfaces 202, 206 to define respective top and bottom surfaces 210 (FIG. 4), 212, as well as opposed side surfaces 214 (FIG. 4), 216. As illustrated in FIG. 2, the top and bottom surfaces 210, 212, engage side surfaces 214, 216, respectively, to provide a substantially quadrilateral cross-section with rounded corners 218 on an upper end thereof. Although lower body 200 is illustrated as having rounded corners 218 extending around the entire perimeter thereof, it is contemplated that only the intersection of the proximal and distal end surfaces 202, 206 and bottom surface 212 includes rounded corners 218. Bottom surface 212 is generally shown as approximating top surface 210 in a direction from trailing end 208 to leading end 204 (FIG. 5); however, it is contemplated that bottom surface 212 may be parallel to top surface 210. Second lumen 200*a* is defined through top and bottom surfaces 210, 212. Although shown as generally having a complimentary shape to that of first lumen 100*a* of upper body 100, it is contemplated that second lumen 200*a* may have any suitable shape different than that of first lumen 100*a*, such as square, oval, circular, or the like.

Continuing with FIG. 2, bottom surface 212 defines a plurality of ridges 220 arranged thereon. Ridges 220 are configured to frictionally engage an adjacent surface of a vertebral body (i.e., a vertebral endplate) to maintain expandable spinal implant 10 in a position relative to the adjacent vertebral body and to inhibit expandable spinal implant 10 from backing out of the intervertebral space since the ridges 220 will bite into the adjacent vertebral endplate.

Figure 4:
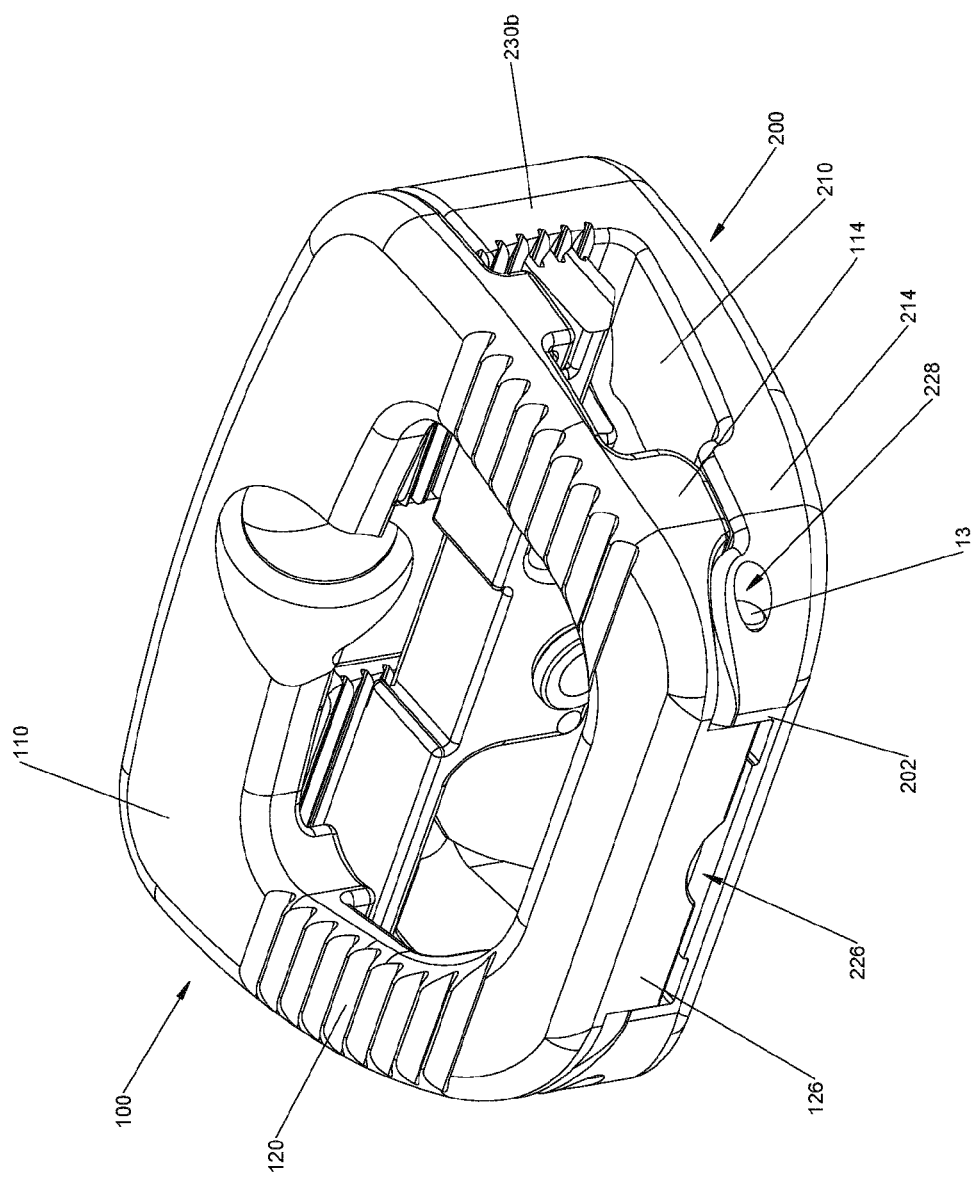
FIG. 4 is a front, perspective view of the expandable spinal implant of FIG. 1.

As illustrated in FIG. 4, slot 226 is defined within top surface 210 adjacent to proximal end surface 202. Slot 226 is centrally located between side surfaces 214, 216 (FIG. 2) and extends normal from proximal end surface 202 such that hinge 126 may be disposed therein. Aperture 228 is defined through each of side surfaces 214, 216 adjacent to leading end 204 and is configured and/or adapted to receive hinge pin 13. One end of aperture 228 is dimensioned to rotatably support hinge pin 13 while the opposing end of aperture 228 is dimensioned to frictionally engage hinge pin 13, thereby capturing hinge pin 13 therein and permitting upper body 100 and lower body 200 to be articulated relative to each other about hinge pin 13 from a closed, approximated position, to a plurality of open (articulated) positions.

Opposing lugs 230*a*, 230*b* are disposed on top surface 210 adjacent to each of side surfaces 214, 216 respectively and extend normal therefrom. Opposing lugs 230*a*, 230*b* are separated such that lug 130 may be disposed therein when upper body and lower body are in an approximated configuration. A plurality of teeth 232 is disposed on a leading face of opposing lugs 230*a*, 230*b* and is configured to engage teeth 302 of ratchet 300.

A plurality of screw holes 238 extend through each of opposing lugs 230*a*, 230*b* and have a similar configuration to that of screw hole 138 with lips 238*b*. The interaction between the bone screw 14 and the lip 238*b* is substantially similar to the interaction between the bone screw 14 and the lip 138*b* that was discussed hereinabove. Therefore, in the interest of brevity, screw holes 238 will not be described in detail herein. It is contemplated that the plurality of screw holes 138, 238 may include a locking device (not shown) to retain bone screw 14 therein. The locking device may be any suitable locking device, such as a locking clip, locking plate, an additional screw, or the like. For a detailed discussion of the construction of exemplary locking devices, reference may be made to U.S. patent application Ser. No. 13/750,496 and U.S. Pat. No. 8,137,405, the entire contents of each which are incorporated herein by reference.

Figure 9:
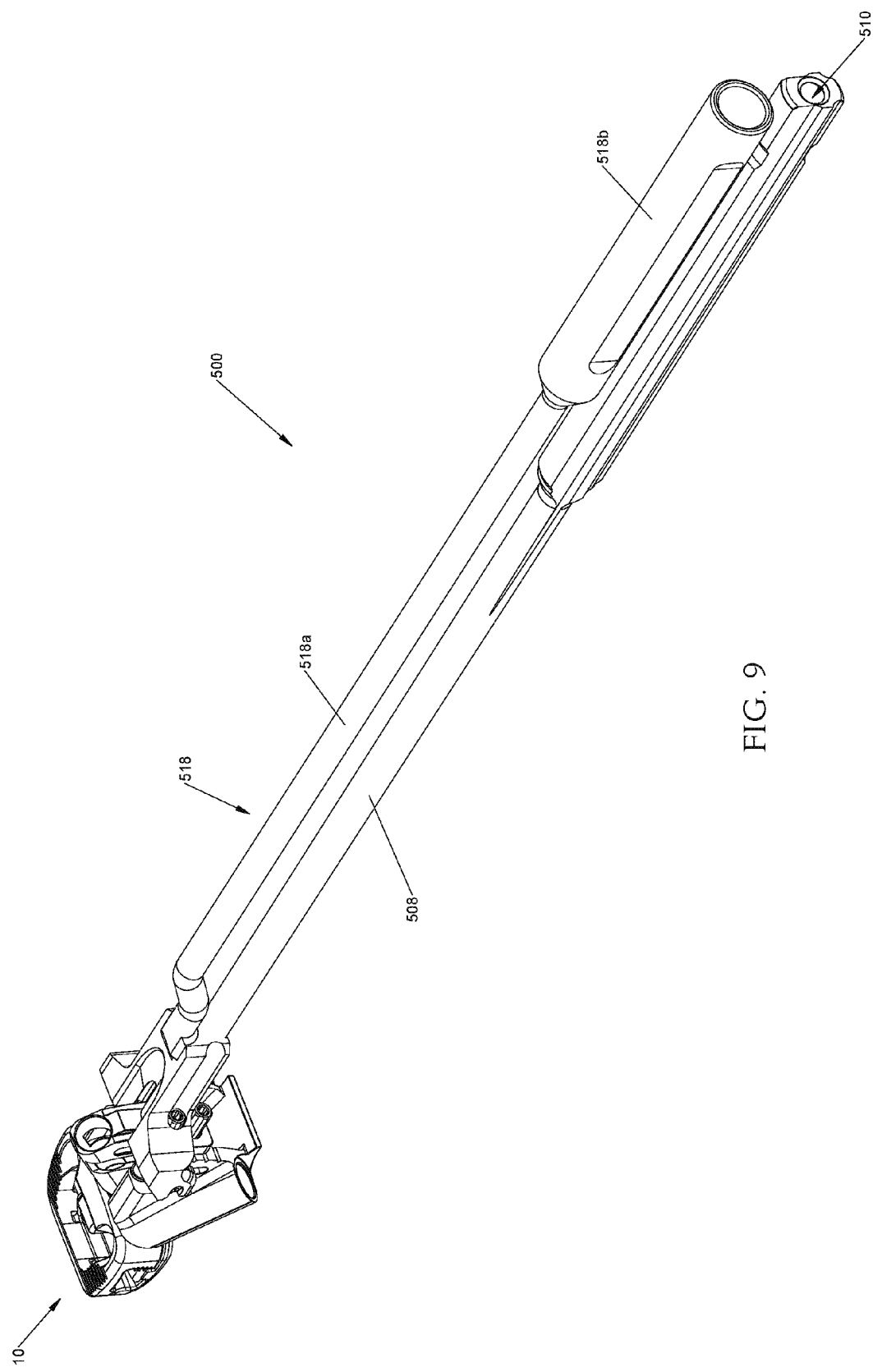
FIG. 9 is a rear, perspective view, of the insertion instrument of FIG. 7, including an articulating bar, coupled to the expandable spinal implant of FIG. 1.

A plurality of threaded bores 240 (FIG. 2) is defined through second end surface 206 on each of opposing lugs 230*a*, 230*b* respectively. Threaded bores 240 are configured and/or adapted to engage guide screws 502 of insertion instrument 500 (FIG. 9).

Figure 3:
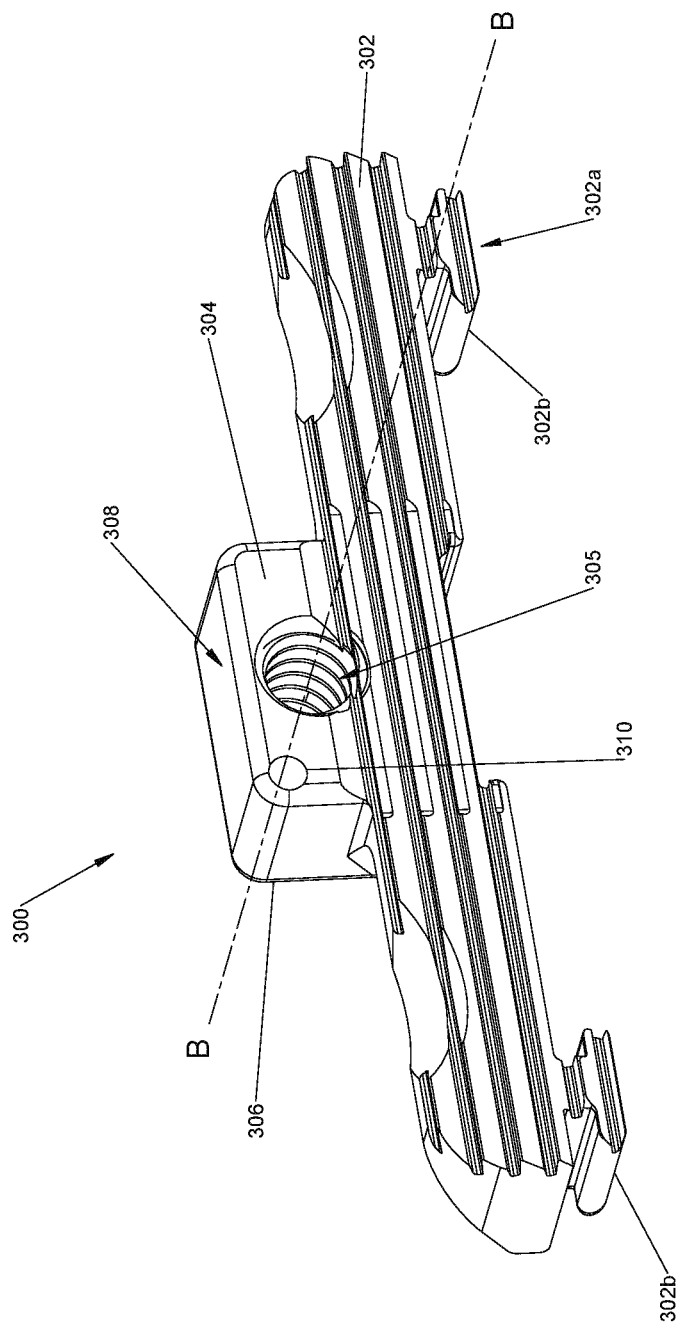
FIG. 3 is a perspective view of a ratchet mechanism of the expandable spinal implant of FIG. 1.

With reference to FIGS. 2 and 3, an illustration of ratchet 300 is shown having a generally T-shaped configuration. Threaded through-hole 305 extends through leg 308 and defines longitudinal axis B-B. Ratchet 300 is oriented relative to upper body 100 such that longitudinal axis B-B is coaxial with longitudinal axis A-A. Threaded through-hole 305 is configured to threadably engage threaded shank 400*b* of ratchet screw 400 such that ratchet 300 may be translated axially along axis B-B as ratchet screw 400 is rotated. Teeth 302 are disposed on a trailing edge 304 of ratchet 300 and are configured and/or adapted to engage teeth 232 of lower body 200 as ratchet 300 is advanced axially along axis A-A toward the leading face of opposing lugs 230*a*, 230*b*. Once engaged, teeth 302 and 232 maintain lower body 200 and upper body 100 in a selected position relative to each other.

Locating bore 310 extends through leg 308 and is configured to receive locating pin 12 such that ratchet 300 is translatably supported thereon. Locating bore 310, in conjunction with locating pin 12 and channel 142 (FIG. 2A) of upper body 100, serves to locate ratchet 300 relative to upper body 100 to maintain the coaxial alignment of axes A-A and B-B.

A pair of legs 302*a* is disposed on opposing sides of the underside of ratchet 300. Legs 302*a* extend normal from the underside of ratchet 300 and have a generally T-shaped configuration, complimentary to T-shaped channel 142 of upper body 100, defining feet 302*b*. Feet 302*b* are configured to engage tabs 122*a*, 122*b*, 122*c*, and 122*d* of upper body 100 such that ratchet 300 is translatably supported along axis B-B. In conjunction with locating pin 12, T-shaped channel 142 (FIG. 2A) and feet 302*b* translatably support ratchet 300 such that ratchet 300 may translate along axis B-B relative to upper body 100 and locating pin 12. In this manner, T-shaped channel 142 and feet 302*b* translatably support the lower side of ratchet 300, while locating bore 310 and locating pin 12 translatably support the upper side of ratchet 300, thereby maintaining coaxial alignment of axes A-A and B-B and preventing any binding that may occur during translation of ratchet 300 relative to upper body 100.

Referring now to FIG. 2, an illustration of ratchet screw 400 is illustrated having proximal and distal ends, includes a head 400a on the proximal end and a threaded shank 400b extending distally therefrom. Head 400a of ratchet screw 400 defines a tool-engaging recess 400c. Tool-engaging recess 400c may have any shape and/or dimension suitable for transmitting rotational motion from a tool to ratchet screw 400 (e.g., square, hex, pozidrive, or the like). Ratchet screw 400 is configured to be threaded into threaded bore 305 of ratchet 300. Flange 402 is disposed adjacent to head 400a and is configured to engage annular groove 136 of lug 130 such that ratchet screw 400 is rotatably supported within annular groove 136 thereby causing ratchet 300 to translate axially in a first direction along axis B-B as ratchet screw 400 is rotated in a first direction. The distal end of ratchet screw 400 includes an unthreaded portion 404 disposed on the shank configured to engage washer 11. Washer 11 is configured and/or dimensioned to be advanced over the unthreaded portion 404 of ratchet screw 400 and engage the leading edge of ratchet 300 such that when ratchet screw 400 is rotated in a second direction, washer 11 abuts the leading edge of ratchet 300 and advances ratchet 300 axially in a second direction along axis B-B. Washer 11 is retained on the unthreaded portion 404 of ratchet screw 400 by any means known in the art, such as bonding, welding, etc.

Figure 6B:
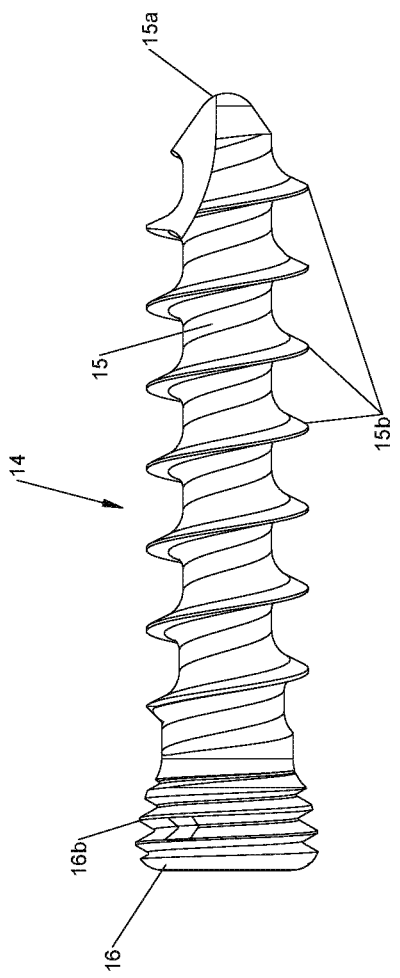
FIG. 6B is a side view of the bone screw of FIG. 6A.
Figure 6C:
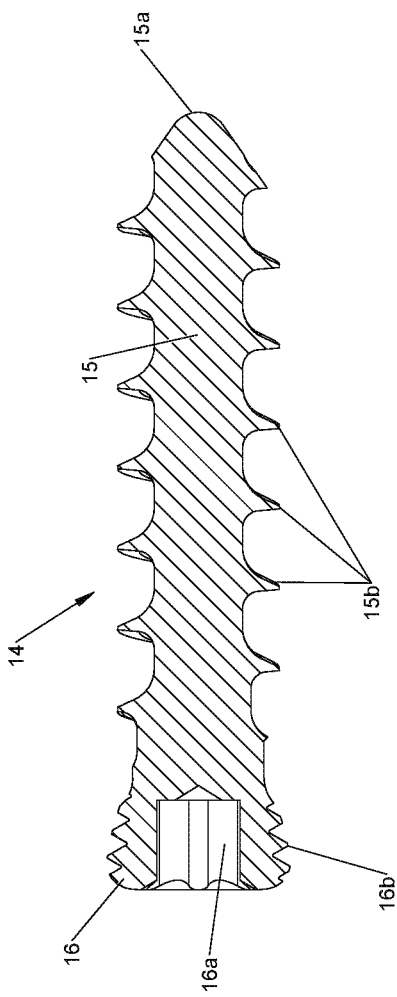
FIG. 6C is a side, cross-sectional view of the bone screw of FIG. 6A.
Figure 6A:
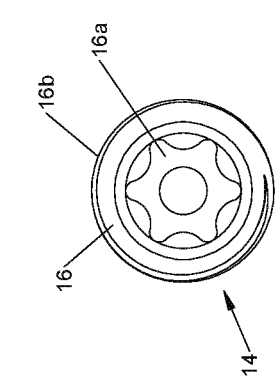
FIG. 6A is a top view of a bone screw usable with the expandable spinal implant of FIG. 1.

Referring now to FIGS. 6A-C, an illustration of bone screw 14 configured for use with expandable spinal implant 10 is shown. As can be appreciated, a plurality of bone screws 14 is configured to secure each of upper and lower bodies 100, 200 of expandable spinal implant 10 to adjacent vertebral bodies. However, as bone screws 14 are similar to one another, only one is described in detail herein. It is also contemplated that other suitable bone screws 14 be provided for use with expandable spinal implant 10.

Bone screw 14 generally includes a shank 15 and a head 16. Shank 15 defines a distal tip 15a and pitched threading 15b disposed about shank 15. Distal tip 15a and pitched threading 15b facilitate driving bone screw 14 into bone and securement of bone screw 14 therein. Head 16 of bone screw 14 defines a tool-engaging recess 16a. Head 16 further includes a thread 16b for threadably engaging lip 138b, 238b of upper and lower bodies 100, 200 respectively. Pitched threading 15a has a pitch greater than that of thread 16b. Tool-engaging recess 16a may have any shape and/or dimension suitable for transmitting rotational motion from a tool to bone screw 14 (e.g., square, hex, pozidrive, or the like).

For a detailed discussion of the construction of exemplary bone screws, reference may be made to U.S. patent application Ser. No. 13/750,496 as referenced hereinabove.

With reference to FIGS. 7-11, an insertion instrument 500 provided in accordance with the present disclosure is illustrated. Insertion instrument 500 includes first body 504 and second body 506, which are pivotably connected at a first end such that first and second body 504, 506 are operable to be positioned in an expanded state (FIG. 11), or an approximated state (FIG. 7). First body 504 includes an elongate handle 508 extending proximally therefrom, defining a tool lumen 510 therethrough (FIG. 9). Tool lumen 510 is adapted to receive any suitable tool (not shown) capable of engaging tool engaging recess 400c of ratchet screw 400 for transmitting rotational motion thereto.

Guide bores 512 are defined through first body 504 and second body 506, and are arranged at corresponding angles to that of screw holes 138, 238 such that when insertion instrument 500 is secured to expandable spinal implant 10, bone screws 14 may be advanced through guide bores 512 and thereafter, screw holes 138, 238.

Figure 10:
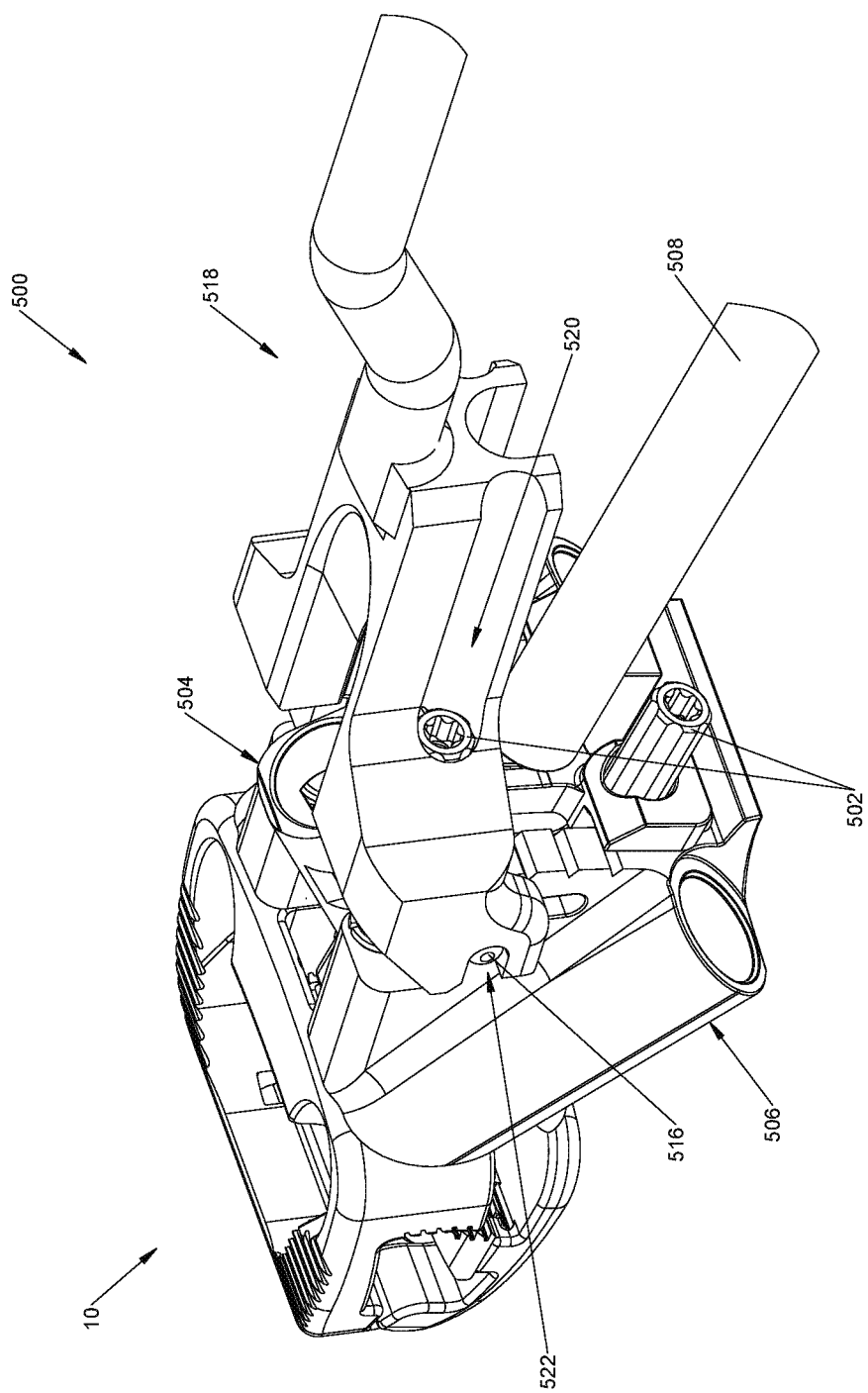
FIG. 10 is a rear, perspective view, of the distal end of the insertion instrument of FIG. 9 coupled to the expandable spinal implant of FIG. 1.

Guide screws 502 are insertable through corresponding through-bores (not shown) of first and second bodies 504, 506, and are adapted to be threadably received within corresponding threaded bores 140a, 240 of upper and lower bodies 100, 200 respectively. Guide pins 516 are disposed on opposing side surfaces of second body 506 and are configured to engage slots 522 of upper handle 518 (FIG. 10). Upper handle 518 is selectably engageable with guide pins 516 and guide screws 502 of second body 506. Apertures 520 are defined through a distal end of upper handle 518 and are configured to receive guide screws 502 of second body 506 therein. Slots 522 are disposed on opposing side surfaces of the distal end of upper handle 518 and are configured to receive guide pins 516 therein. Upper handle 518 includes an elongate body 518a extending proximally and terminating at a proximal end 518b, such that a clinician may grasp the proximal end 518b of upper handle 518 and the proximal end of elongate handle 508 and manipulate upper handle 518 and elongate handle 508 relative to each other. Upper handle 518, guide screws 502, and slots 522 cooperate to allow a clinician to manipulate upper handle 518 and elongate handle 508 relative to each other to effectuate expansion of expandable spinal implant 10.

Figure 12:
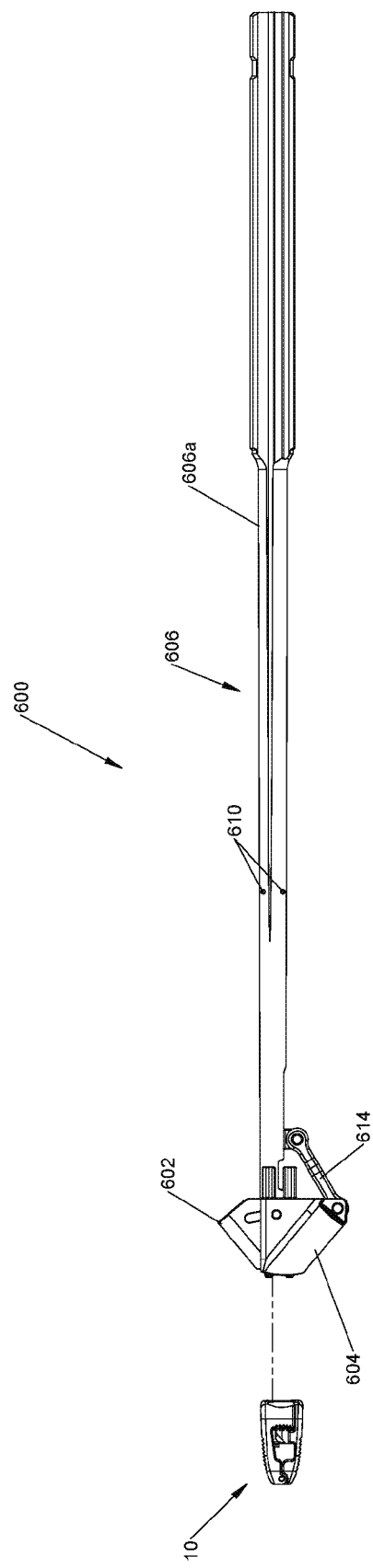
FIG. 12 is a side view of an alternate embodiment of the insertion instrument of FIG. 7 and the expandable spinal implant of FIG. 1 in accordance with the present disclosure.
Figure 13:
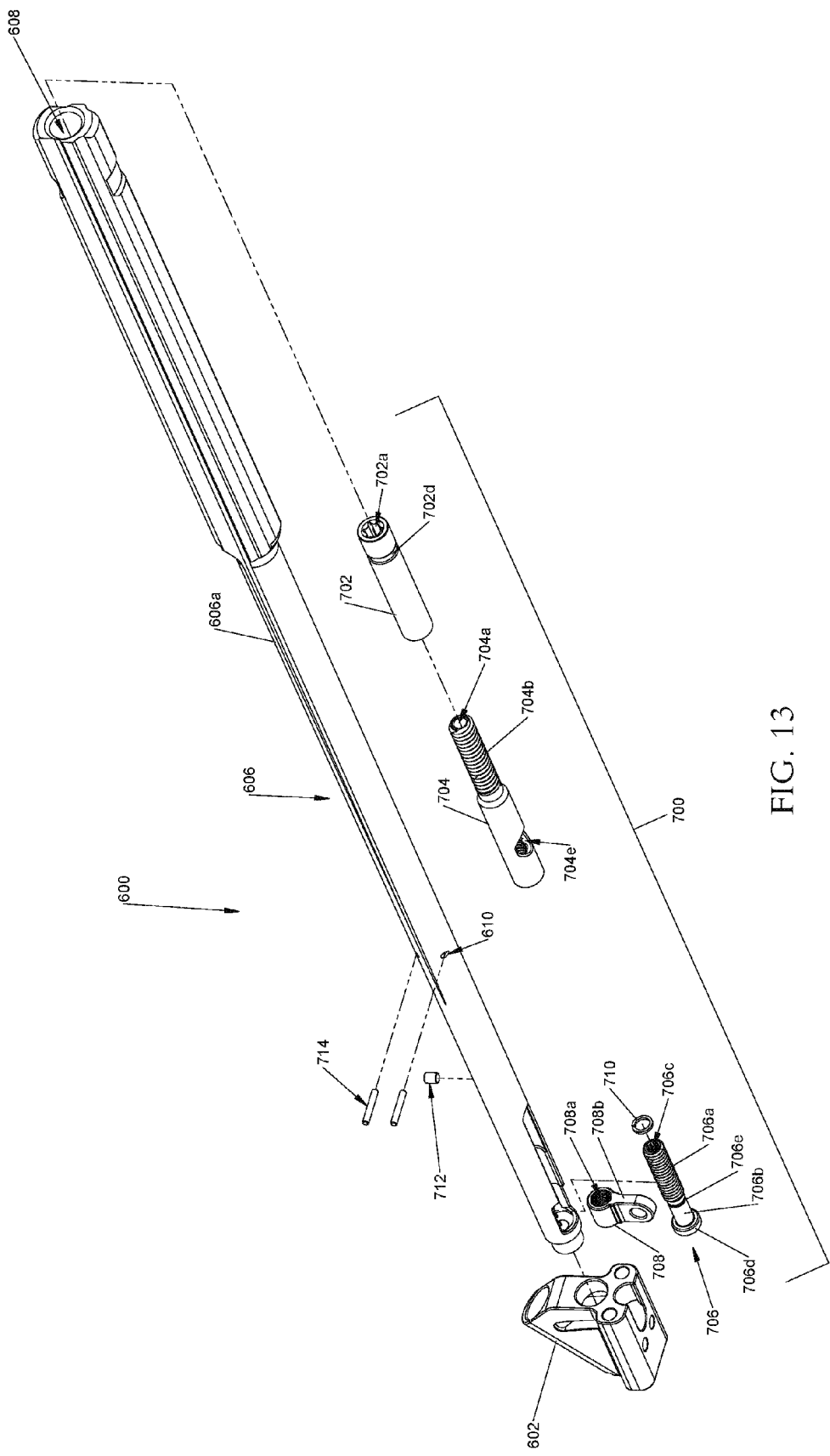
FIG. 13 is a rear, perspective view, of the insertion instrument of FIG. 12, with parts separated.

With references to FIGS. 12-18, an alternate embodiment of an insertion instrument is generally designated as insertion instrument 600. In this embodiment, insertion instrument 600 includes first body 602 and second body 604, which are operable to be positioned in an expanded state (FIG. 18), or an approximated state (FIG. 17). First body 602 includes an elongate handle 606 extending proximally therefrom, defining a lumen 608 therethrough (FIG. 13). Locating bores 610 are defined through an outer surface 606a and a portion of an inner surface of lumen 608 of elongate handle 606 in a direction normal to lumen 608. Locating bores 610 are adapted to frictionally retain locating pins 714 such that locating pins 714 are flush with the outer surface 606a. Locating pins 714 may be any suitable pin, such as a dowel, a roll pin, a rivet, or the like. Through-hole 612 (FIG. 14) is defined through outer surface 606a and is adapted to frictionally retain limiting pin 712. Limiting pin 712 may be any suitable pin, such as a dowel, a roll pin, a rivet, or the like.

Figure 14:
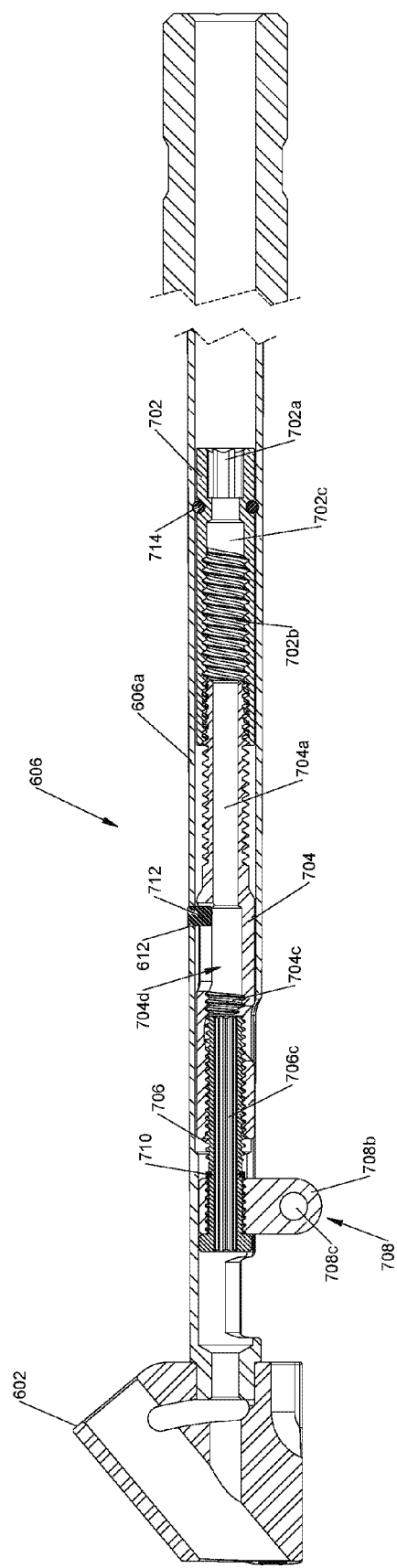
FIG. 14 is a side, cross-sectional view, of the insertion instrument of FIG. 12.
Figure 15:
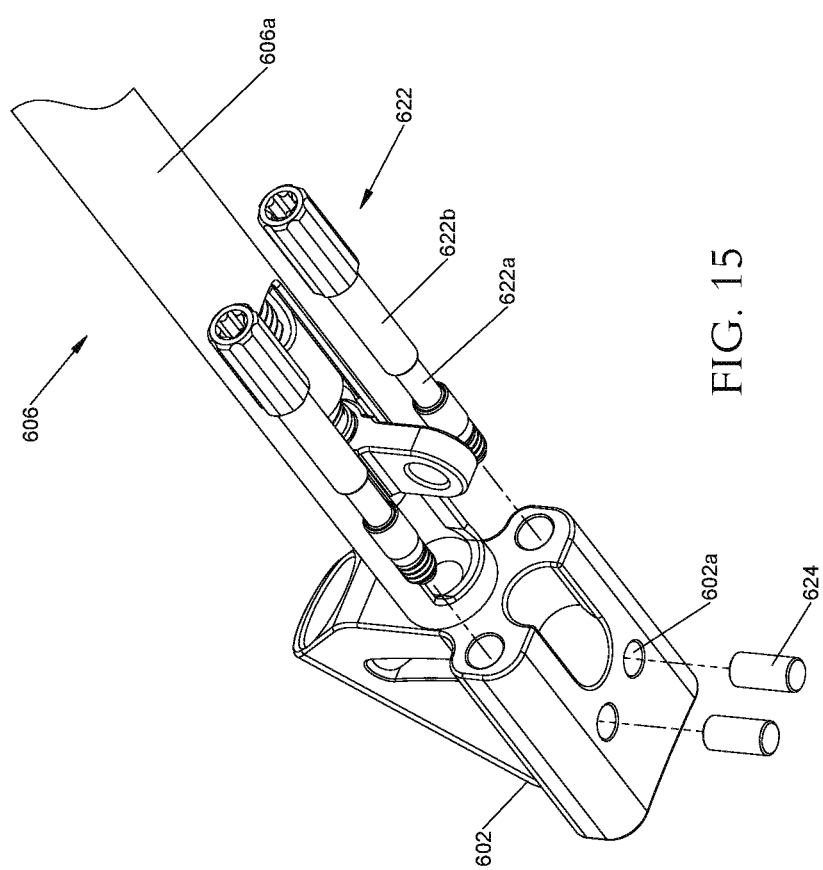
FIG. 15 is a bottom, perspective view, of the distal end of the insertion instrument of FIG. 12, with parts separated.

As illustrated in FIGS. 13 and 14, adjustment assembly 700 is disposed within lumen 608 and generally includes an adjustment nut 702, a coupler 704, a threaded barrel 706, a shuttle 708, a retaining clip 710, limiting pin 712, and locating pins 714. Adjustment nut 702 is adapted to be received within lumen 608 and includes a tool receiving portion 702a defined within a proximal end thereof. Internal threads 702b are disposed on an interior surface of the distal end of a throughbore 702c defined through adjustment nut 702. An outer surface of adjustment nut 702 includes an annular groove 702d defined thereon adapted to receive a portion of locating pins 714. When locating pins 714 are advanced within locating bores 610 and annular groove 702d, adjustment nut 702 is rotatably retained within lumen 608 (i.e., adjustment nut 702 is free to rotate while being fixed longitudinally).

Coupler 704 includes a through-hole 704a defined through proximal and distal ends. The proximal end of coupler 704 includes a threaded outer surface 704b adapted to threadably engage internal threads 702b of adjustment nut 702. The distal end of coupler 704 includes threads 704c disposed on an inner surface of through-hole 704a. A first slot 704d is defined through an outer surface of coupler 704 and extends longitudinally along through-hole 704a. A second slot 704e is defined through an opposing side of the outer surface of coupler 704 and extends longitudinally along through-hole 704a. First slot 704d is adapted to slidably receive limiting pin 712 such that when coupler 704 is translated along lumen 608 by rotation of adjustment nut 702, limiting pin 702 abuts the proximal or distal end of first slot 704d, thereby limiting the longitudinal motion of coupler 704.

Shuttle 708 includes a threaded bore 708a defined therethrough and a flange 708b extending normally therefrom. Threaded bore 708a is adapted to be rotatably supported on shank 706b of threaded barrel 706. Threaded barrel 706 includes a threaded outer surface 706a disposed on a proximal end thereof and a hexagonal through-bore 706c defined therethrough. Hexagonal through-bore 706c is adapted to engage a suitable tool capable of effectuating rotational motion. Threaded barrel 706a transitions to a smooth shank 706b located on a distal end of threaded barrel 706. Smooth shank 706b transitions to a flange 706d having a diameter greater than that of smooth shank 706b. Retaining clip 710 is disposed within an annular groove 706e defined in an outer surface of smooth shank 706b. Retaining clip 710 may be any suitable clip, such as a circlip, a spring clip, or the like. Shuttle 708 is longitudinally retained between flange 706d and retaining clip 710. Threaded outer surface 706a is adapted to threadably engage threads 704c of coupler 704. Once entirely threaded therein, the proximal end of threaded outer surface 706a is mechanically secured to threads 704c by any suitable means, such as staking, welding, or the like.

Link 614 includes a first transverse pivot hole 614a defined through opposing sides of a distal end thereof. A channel 614b is defined through a proximal end of link 614 and is adapted to slidably receive flange 708b therein. A second transverse pivot hole 614c is defined through opposing sides of a proximal end of link 614.

First and second bodies 602, 604 are similar to first and second bodies 504, 506, respectively, and therefore, in the interest of brevity, only the differences therebetween will be described in detail herein.

Figure 16:
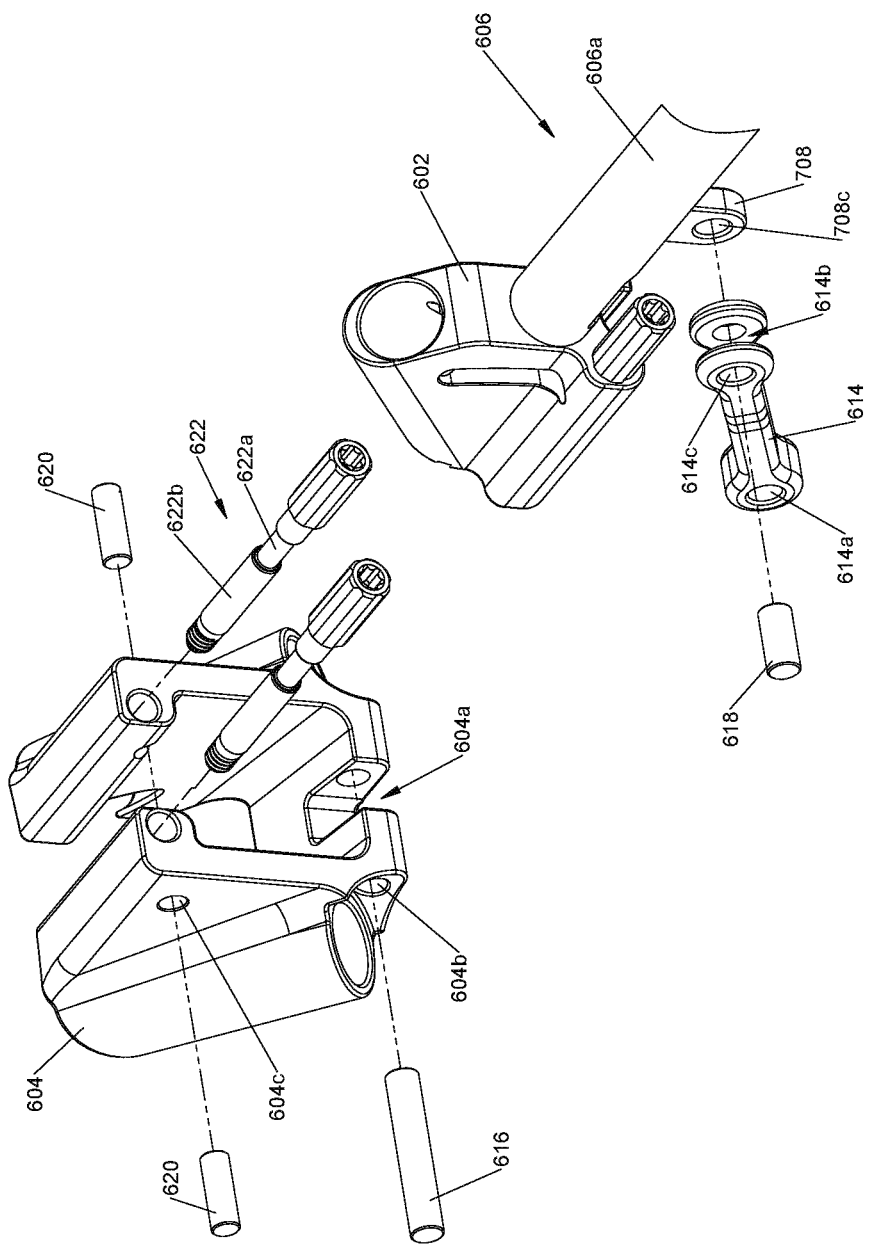
FIG. 16 is a rear, perspective view, of the distal end of the insertion instrument of FIG. 12, with parts separated.

As illustrated in FIG. 16, second body 604 includes a slot 604a defined through a proximal end thereof adapted to slidably receive a distal end of link 614. Retaining bores 604b are disposed through side surfaces of second body 604 and are adapted to frictionally receive a first link pin 616. When first link pin 616 is fully advanced within retaining bores 604b and pivot hole 614a, link 614 is rotatably secured to second body 604. A second link pin 618 is adapted to be received within a pivot hole 708c defined through flange 708b and second transverse pivot hole 614c of link 614 such that link 614 is rotatably supported thereon. A pair of transverse through-bores 604c is defined through opposing side surfaces of second body 604 and are adapted to frictionally receive a corresponding first pair of pins 620. Pins 620 are adapted to partially engage a respective annular groove 622a disposed on a shank 622b of retaining screws 622 and may be any suitable pin, such as a dowel pin, a roll pin, a rivet, or the like. Retaining screws 622 are similar to guide screws 502 except for annular groove 622a. When fully inserted, retaining screws 622 are longitudinally fixed by pins 620 while still permitting retaining screws 622 to rotate axially.

First body 602 includes a pair of holes 602a disposed within a lower surface thereof. Holes 602a are adapted to receive a corresponding second pair of pins 624. Pins 624 are adapted to partially engage a respective annular groove 622a disposed on a shank 622b of retaining screws 622 and may be any suitable pin, such as a dowel pin, a roll pin, a rivet, or the like. When fully inserted, retaining screws 622 are longitudinally fixed by pins 624 while still permitting retaining screws 622 to rotate axially.

Elongate handle 606, guide screws 502, link 614, and adjustment assembly 700 cooperate to allow a clinician to effectuate expansion of expandable spinal implant 10 as will be discussed in further detail herein.

Figure 5:
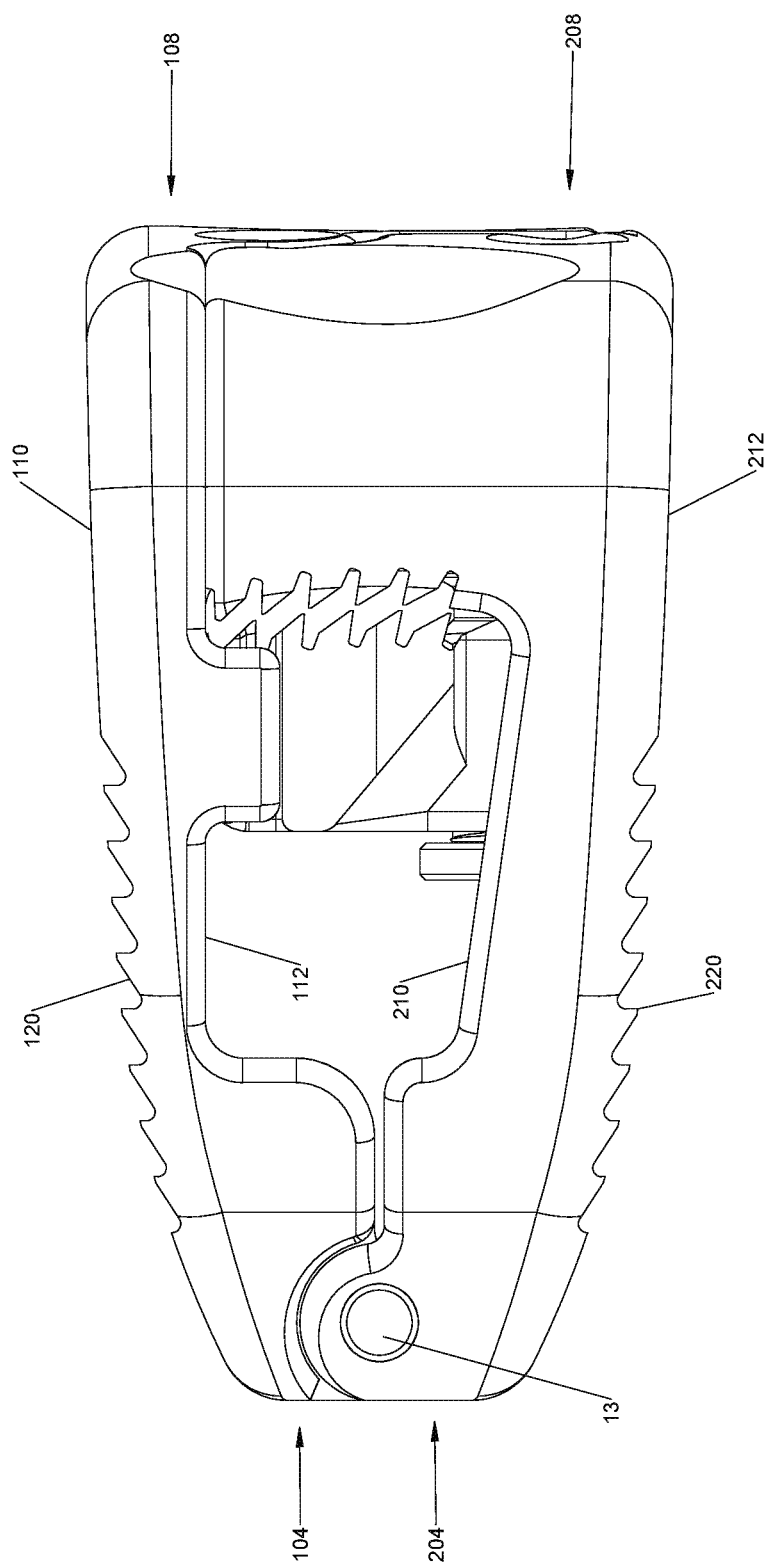
FIG. 5 is a side view of the expandable spinal implant of FIG. 1.
Figure 8:
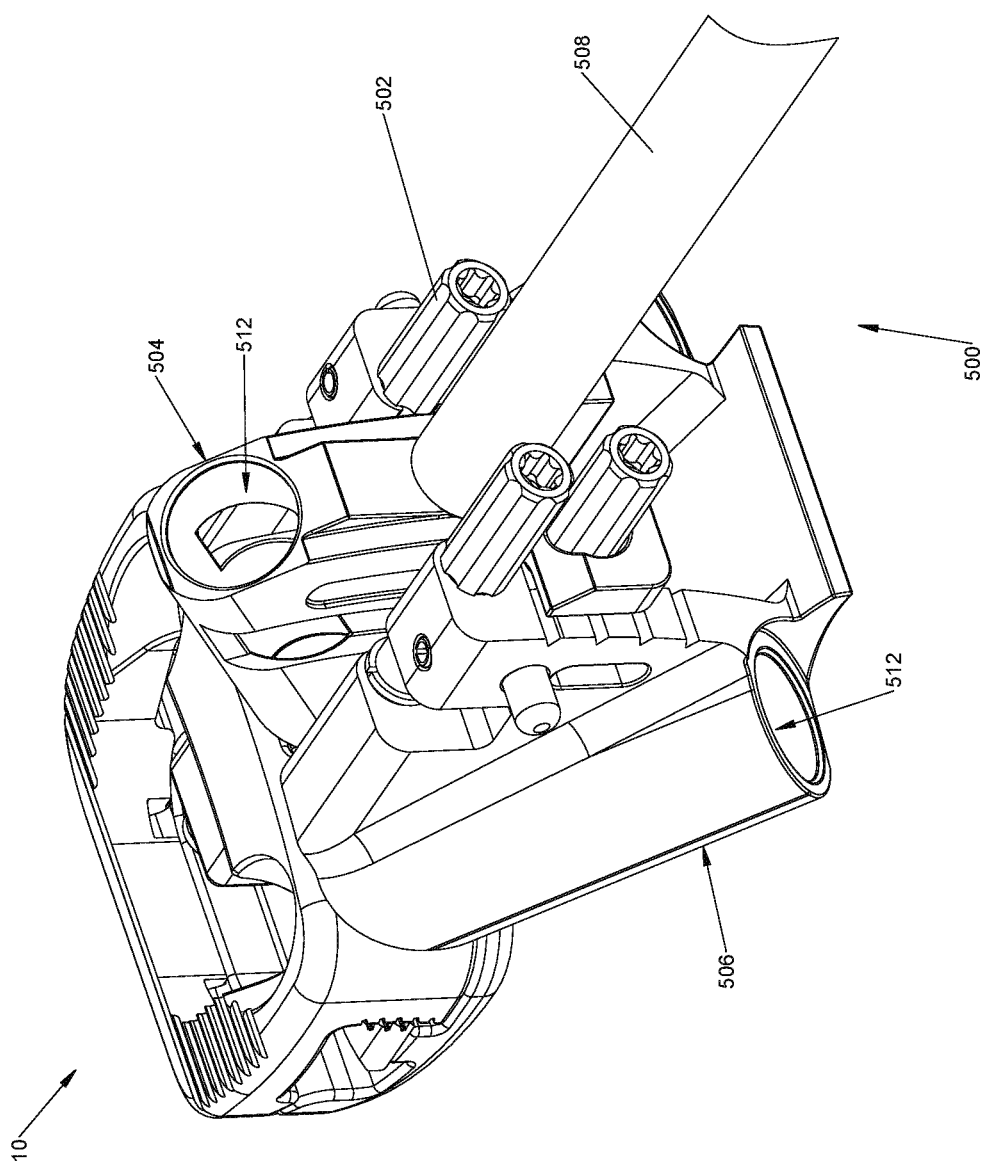
FIG. 8 is a rear, perspective view, of the distal end of the insertion instrument of FIG. 7 coupled to the expandable spinal implant of FIG. 1.
Figure 11:
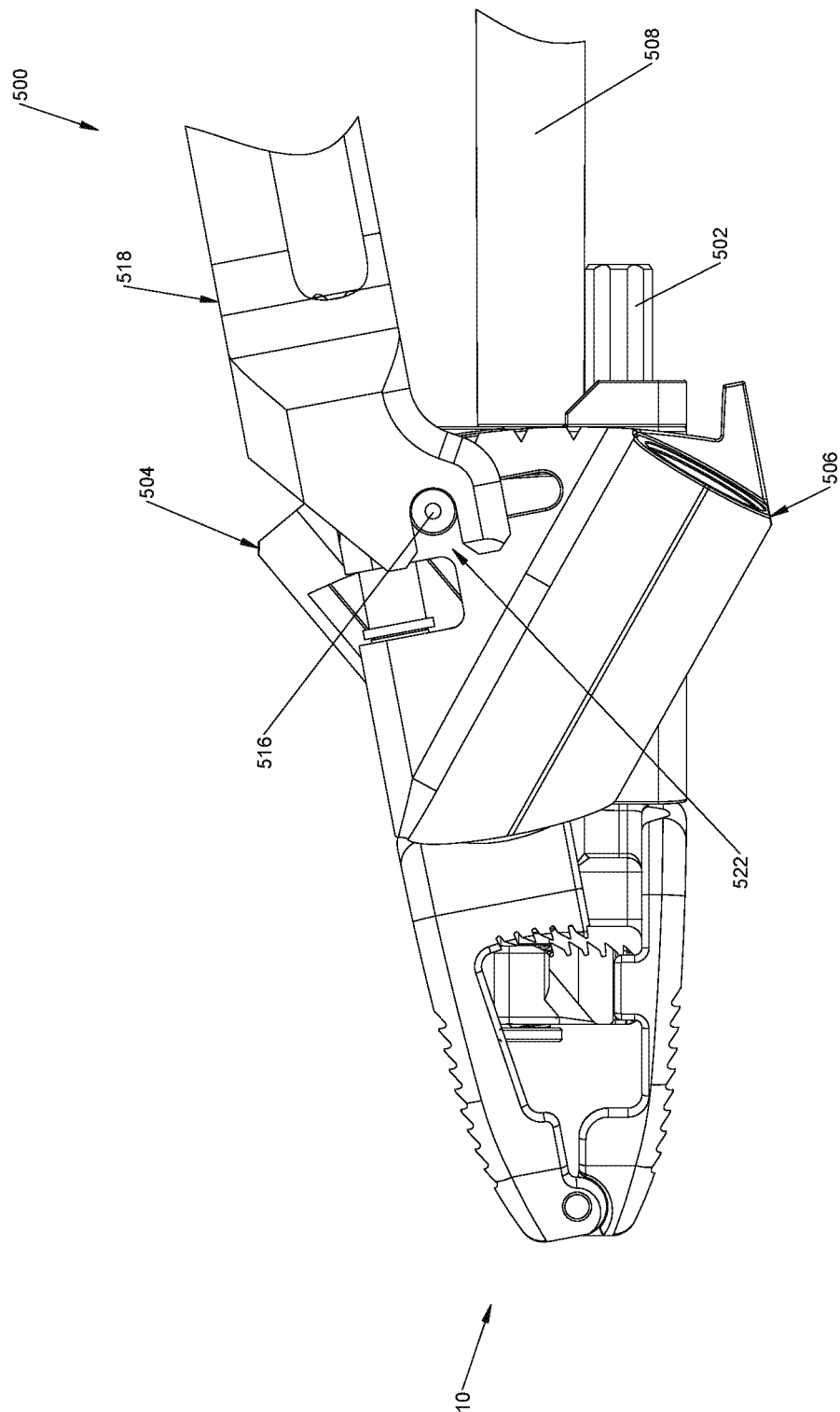
FIG. 11 is a side view of the distal end of the insertion instrument of FIG. 10 coupled to the expandable spinal implant of FIG. 1.

With reference to FIGS. 2 and 5, the insertion of an expandable spinal implant 10 into the intervertebral space between adjacent vertebral bodies during the course of a spinal surgical procedure is described. Initially, ratchet 300 is placed in a first, unengaged position by rotating ratchet screw 400 in a first direction using a suitable tool inserted within tool-engaging recess 400c of ratchet screw 400. Next, upper body 100 is manipulated relative to lower body 200 such that upper body and lower body 100, 200 are in a first, approximated, position. At this point, ratchet screw 400 is rotated in a second, opposite direction, drawing teeth 302 of ratchet 300 into engagement with teeth 232 of lower body 200 such that the position of upper body 100 relative to lower body 200 is fixed. The intervertebral space is then prepared, e.g., damaged or diseased tissue is removed. Thereafter, the interior space of lumens 100a, 200a of upper and lower body 100, 200, respectively, may be packed with bone in-growth material, drugs, or other suitable materials or compounds. Examples of such materials are allograft material, autograft material, calcium phosphate/bone marrow aspirate (BMA), autogenous bone material, or synthetic materials comprised of a biocompatible, osteoconductive, osteoinductive, or osteogenic material such as VITOSS® Synthetic Cancellous Bone Void Filler material. Next, expandable spinal implant 10 is affixed to a insertion instrument 500 by threadably engaging guide screws 502 to threaded bores 140a, 240 disposed on upper body 100 and lower body 200 respectively (FIGS. 7-8). At this point, expandable spinal implant 10 may be advanced within an incision within the patient and thereafter, a previously prepared intervertebral space of the patient's spine. Bone screws 14 (FIGS. 6A-6C) are then inserted through guide bores 512 of insertion instrument 500 (FIG. 8), and thereafter, screw holes 238 of lower body 200 and are driven into one of the adjacent vertebral bodies. Due to the obliquely angled configuration of screw holes 238 relative to second end face 206 mentioned above, bone screws 14 are guided through screw holes 238 and into the vertebral body. Next, a final bone screw 14 is inserted through remaining guide bore 512 of insertion instrument 500, and thereafter, screw hole 138 of upper body 100 and is driven into the other adjacent vertebral body. As with screw holes 238, the obliquely angled configuration of screw hole 138 relative to second end face 106 guides bone screw 14 through screw hole 138 and into the vertebral body. Next, a suitable tool may be advanced within tool lumen 510 (FIG. 9) of insertion tool 500 and thereafter ratchet screw 400. Ratchet screw 400 may be rotated in the first direction to disengage teeth 302 of ratchet 300 from teeth 232 of lower body 200. At this point, upper body 100 and lower body 200 may be articulated about hinge pin 13 to a desired location by manipulating upper handle 518 and elongate handle 508 relative to each other (FIG. 11). Articulation of upper body 100 and lower body 200 relative to each other effectuates lordosis of the spine. Alternatively, it is contemplated that upper body 100 and lower body 200 may be articulated relative to each other to effectively fill the intervertebral space without effectuating lordosis of the spine. The desired location of upper body 100 and lower body 200 is selected based on the desired lordosis of the spine. Once a desired location has been selected, ratchet screw 400 is rotated in the second, opposite, direction to draw teeth 302 of ratchet 300 into engagement with teeth 232 of lower body 200 to lock the position of upper body 100 relative to lower body 200. Thereafter, insertion instrument 500 is disengaged from expandable spinal implant 10 and removed from the incision.

In another embodiment, alternate insertion instrument 600 may be secured to expandable spinal implant 10 by threading retaining screws 622 into threaded bores 140a, 240 (FIGS. 2 and 2A) disposed on upper body 100 and lower body 200 respectively (FIG. 12). The insertion, locking, and removal of expandable spinal implant 10 using insertion instrument 600 is similar to that using insertion instrument 500, and therefore, in the interest of brevity, only the differences will be described herein.

Once expandable spinal implant 10 has been inserted within the intervertebral space, a first suitable tool (not shown) is inserted within lumen 608 of elongate handle 606 and is drawn into engagement with the tool receiving portion 702a of adjustment nut 702. Adjustment nut 702 is then rotated, which, in turn, draws coupler 704 in a proximal direction within lumen 608 of elongate handle 606. As coupler 704 is drawn proximally, threaded barrel 706, and therefore shuttle 708 are also drawn proximally, causing link 614 to impart a proximal force on second body 604 thereby causing second body 604 to rotate relative to first body 602. This rotation of second body 604 effectuates expansion of expandable spinal implant 10 (see FIGS. 17 and 18). Once a desired location of upper body 100 and lower body 200 is selected, the first tool is removed from lumen 608. Next, a second suitable tool may be advanced within lumen 608 of insertion tool 600 and advanced through through-hole 704a of coupler 704, through-bore 706c of threaded barrel 706, and thereafter ratchet screw 400.

In some embodiments, the position of upper body 100 relative to lower body 200 may be set prior to inserting expandable spinal implant 10 within the intervertebral space. Thereafter, the position may continue to be manipulated until the desired lordosis is achieved using the procedure previously described above.

It is further contemplated that the teeth 302 of ratchet 300 may be drawn into engagement with teeth 232 of lower body 200 such that lower body 200 may be articulated about hinge pin 13 in a first direction (i.e., ratchet open), but not in a second direction (i.e., preventing upper body 100 and lower body 200 from approximating). Once the desired lordosis is achieved, ratchet screw 400 may be rotated in the second direction to lock upper body 100 and lower body 200 in the selected position.

This process may be repeated as many times as the procedure requires, whether it be for the same expandable spinal implant 10 or for a plurality of expandable spinal implants 10 as required by the procedure being performed.

It will be understood that various modifications may be made to the embodiments of the presently disclosed expandable spinal implant. Therefore, the above description should not be construed as limiting, but merely as exemplifications of embodiments. Those skilled in the art will envision other modifications within the scope and spirit of the present disclosure.

What is claimed is:

1. A method of performing surgery, comprising:
positioning an upper body and a lower body of a spinal implant in a first, approximated position relative to each other, the upper body and lower body pivotably coupled at a first end and capable of movement relative to each other, wherein each of the upper body and the lower body is dimensioned to be installed between first and second vertebral bodies, the outer surfaces of each of the upper body and the lower body are adapted to engage a corresponding end plate of the first and second vertebral bodies;
preparing an intervertebral space between the first and second vertebral bodies to receive the spinal implant;
inserting the spinal implant into the prepared intervertebral space;
articulating the upper body and lower body relative to each other to effectuate a desired lordosis of a spine of the patient;
inserting a plurality of bone screws that are capable of being attached to bone through a plurality of screw holes defined through the outer surface and an adjacent side surface of the upper body and through the outer surface and an adjacent side surface of the lower body, wherein the screw holes are oriented towards a respective adjacent one of the first and second vertebral bodies at an oblique angle; and
locking a ratchet mechanism slidably disposed on one of the upper and lower bodies, to lock the position of the upper body and lower body relative to each other, the ratchet mechanism capable of engaging the opposite one of the upper and lower bodies thereby permitting movement of the upper and lower bodies relative to each other in a first direction, but not in a second direction.

2. The method of claim 1, wherein inserting the spinal implant includes first securing the spinal implant to an insertion device.

3. The method of claim 1, wherein locking the ratchet mechanism includes rotating a ratchet screw disposed within an annular groove defined within the upper body in a first direction, wherein the ratchet screw includes a head and a threaded shank extending therefrom, the ratchet screw being threadably engaged within a threaded through-bore defined through the ratchet mechanism, wherein rotating the ratchet screw effectuates movement of the ratchet mechanism in a first direction thereby causing the ratchet mechanism to engage the lower body and lock the position of the lower body relative to the upper body.

4. The method of claim 1, wherein positioning the upper body and lower body in a first, approximated, position includes engaging a first plurality of teeth defined on a surface of the ratchet mechanism with a second plurality of teeth defined on an opposing surface of the lower body, thereby permitting articulation of the upper body relative to the lower body in a first direction, but not in a second direction.

5. The method of claim 4, wherein locking the ratchet mechanism further includes further rotating the ratchet screw the first direction, thereby causing the first and second pluralities of teeth to further engage, thereby locking the position of the upper body and the lower body relative to each other.

6. The method of claim 1, further including packing a lumen defined in each of the upper body and lower body with bone in-growth material.

7. The method of claim 1, further including packing a lumen defined in each of the upper body and lower body with drugs.

8. The method of claim 1, wherein positioning the upper body and lower body includes positioning the upper body and lower body in a desired articulated position relative to each other.

* * * * *